US009526789B2

(12) United States Patent
Park et al.

(10) Patent No.: US 9,526,789 B2
(45) Date of Patent: Dec. 27, 2016

(54) HIGHLY ROBUST FAST-DISINTEGRATING TABLET AND PROCESS FOR MANUFACTURING THE SAME

(71) Applicant: SAMYANG BIOPHARMACEUTICALS CORPORATION, Seoul (KR)

(72) Inventors: Sang Yeob Park, Daejeon (KR); Hye Jung Lim, Daejeon (KR)

(73) Assignee: SAMYANG BIOPHARMACEUTICALS CORPORATION, Seoul (KR)

( * ) Notice: Subject to any disclaimer, the term of this patent is extended or adjusted under 35 U.S.C. 154(b) by 0 days.

(21) Appl. No.: 14/369,640

(22) PCT Filed: Dec. 28, 2012

(86) PCT No.: PCT/KR2012/011738
§ 371 (c)(1),
(2) Date: Jun. 27, 2014

(87) PCT Pub. No.: WO2013/100701
PCT Pub. Date: Jul. 4, 2013

(65) Prior Publication Data
US 2014/0364513 A1 Dec. 11, 2014

(30) Foreign Application Priority Data

Dec. 28, 2011 (KR) ........................ 10-2011-0144395

(51) Int. Cl.
A61K 9/16 (2006.01)
A61K 9/20 (2006.01)
A61K 9/36 (2006.01)
A61K 47/26 (2006.01)
A61K 31/366 (2006.01)
A61K 31/4178 (2006.01)
A61K 31/4545 (2006.01)
A61K 31/351 (2006.01)
A61K 47/10 (2006.01)
A61K 9/00 (2006.01)

(52) U.S. Cl.
CPC ............ *A61K 47/26* (2013.01); *A61K 9/1694* (2013.01); *A61K 9/2018* (2013.01); *A61K 9/2054* (2013.01); *A61K 9/2059* (2013.01); *A61K 9/2095* (2013.01); *A61K 31/351* (2013.01); *A61K 31/366* (2013.01); *A61K 31/4178* (2013.01); *A61K 31/4545* (2013.01);

*A61K 47/10* (2013.01); *A61K 9/0056* (2013.01); *A61K 9/1623* (2013.01)

(58) Field of Classification Search
CPC .. A61K 9/0056; A61K 9/1623; A61K 9/1694; A61K 47/10; A61K 47/26
See application file for complete search history.

(56) References Cited

U.S. PATENT DOCUMENTS

| 5,720,974 A | 2/1998 | Makino et al. |
| 5,780,055 A * | 7/1998 | Habib ...................... B01J 13/02 424/464 |
| 5,837,285 A | 11/1998 | Nakamichi et al. |
| 2005/0013857 A1 | 1/2005 | Fu et al. |
| 2006/0115529 A1* | 6/2006 | Jeong ................... A61K 9/0056 424/464 |
| 2010/0104640 A1* | 4/2010 | Jeganathan .......... A61K 9/1635 424/474 |

FOREIGN PATENT DOCUMENTS

| EP | 1 323 417 A1 | 7/2003 |
| EP | 2 368 546 A2 | 9/2011 |
| KR | 10-0642976 B1 | 11/2006 |
| KR | 10-0655627 B1 | 12/2006 |
| KR | 10-2009-0114329 A | 11/2009 |
| KR | 10-2010-0084882 A | 7/2010 |
| WO | WO 2013/100705 A1 | 7/2013 |

OTHER PUBLICATIONS

Bi et al., "Rapidly Disintegrating Tablets Prepared by the Wet Compression Method: Mechanism and Optimization", Journal of Pharmaceutical Sciences, Oct. 1999, vol. 88, No. 10, pp. 1004-1010, see Abstract; pp. 1004 and 1006.
International Search Report, issued in PCT/KR2012/011738, dated Apr. 29, 2013.
Jeong et al., "Material properties for making fast dissolving tablets by a compression method", Journal of Materials Chemistry, 2008, vol. 18, pp. 3527-3535, See pp. 3527-3532.
Extended European Search Report, dated Apr. 30, 2015, for European Application No. 12863897.0.

* cited by examiner

*Primary Examiner* — Mina Haghighatian
(74) *Attorney, Agent, or Firm* — Birch, Stewart, Kolasch & Birch, LLP

(57) ABSTRACT

Disclosed are an oral formulation which disintegrates quickly in the oral cavity; a fast-disintegrating tablet having fast disintegrability and high hardness, and a process for manufacturing the same. In addition, slightly wetted granules for manufacturing said fast-disintegrating tablet and a process for manufacturing the same are disclosed.

12 Claims, No Drawings

HIGHLY ROBUST FAST-DISINTEGRATING TABLET AND PROCESS FOR MANUFACTURING THE SAME

TECHNICAL FIELD

The present invention relates to an oral formulation which disintegrates quickly in the oral cavity; a fast-disintegrating tablet having fast disintegrability and high hardness, and a process for manufacturing the same. In addition, the present invention relates to slightly wetted granules for manufacturing said fast-disintegrating tablet and a process for manufacturing the same. More specifically, the present invention relates to slightly wetted granules comprising a spray-dried mannitol and a sucrose binder, and a process for manufacturing the same; and a fast-disintegrating tablet comprising said slightly wetted granules, and a process for manufacturing the same. The fast-disintegrating tablet comprising the slightly wetted granules of the present invention can be manufactured by conventional pharmaceutical equipment; the manufacturing process is simple; and the product has fast disintegrability as well as high hardness.

BACKGROUND ART

Pill or tablet formulation has been conveniently and practically used for a long time in order to administer a drug to the body. However, it has been known that a surprising number of people have trouble in swallowing pills. In addition, the tablet formulation type is inconvenient for old people who have hand tremors or dysphagia; infants and young children who cannot swallow pills, and thus need to take pills in syrup form or take pills by crushing and mixing them with water; people in a situation in which drinking water is difficult to get, such as while traveling; water-restricted patients (for example, nephropathy patients); patients who lie down continuously, and thus have difficulty in sitting up to take medicine; and the like.

Fast-disintegrating tablets have been developed to improve the above problems. Fast-disintegrating tablet is one type of tablet which disintegrates in the oral cavity in several seconds to several tens of seconds by saliva upon putting the tablet in the mouth, and thus may be taken without water. Fast-disintegrating tablet is known by several names, such as "orally disintegrating tablet," "rapidly melting tablet," "orodispersible tablet," "fast-dissolving tablet," "rapidly eroding tablet," etc. Fast-disintegrating tablet is useful for some mental patients other than the subjects mentioned above; there are cases in which they pretend to eat in front of a nurse, hiding a tablet under his/her tongue, and then spitting out the tablet when the nurse is absent, so fast-disintegrating tablet is a useful dosage form to ensure the administration of medicine.

Ideal fast-disintegrating tablets disintegrate quickly and softly in the oral cavity and have physical properties suitable for production, transportation, packaging, storage, etc.—for example, high hardness and low friability. Unfortunately, fast-disintegrating tablets generally have poor physical properties; on the other hand, tablets with good physical properties generally have poor disintegration. Most commercially available fast-disintegrating tablets find a balance or compromise among these needs; or they focus on one aspect, while the shortages are attributed to consumers—for example, by issuing precautions; or they are supplemented in another way, such as specialty packaging.

The known methods for manufacturing fast-disintegrating tablets include a method using freeze-drying; a method similar to a cotton-candy-making process; a method to contain an appropriate amount of foaming agent in tablets; a method using a large amount of disintegrating agent; a method using an appropriate combination of highly soluble saccharide and highly modable saccharide; a method for improving the physical properties by humidifying or heating the tablet obtained by low-pressure tableting; a method for tableting a mixture which hardly contains a lubricant without problems by using an improved tableting machine in which a lubricant is sprayed into a mold where a tablet is formed; etc.

However, many of the above manufacturing methods require special equipment or high-priced facilities; or general pharmaceutical equipment cannot be used as it is, and thus has to be modified, and which may cause a rise in the production cost or restrict various applications. In addition, the tablets which need a specific humidity and temperature conditions at or after tableting may be exposed to harsh conditions or require unnecessary investments in equipment, which may limit applications.

Korean Patent No. 0642976 discloses a method for manufacturing a fast-disintegrating tablet, comprising tableting after granulating a drug, diluent and saccharide having a relatively low melting point; heating over the melting temperature at which the saccharide having a low melting point is melted; and cooling. However, the method includes a heating step, wherein the formed tablet is placed in a 120-160° C. oven for several minutes, and thus has a limitation in that it cannot be used for drugs unstable to high temperature.

Korean Patent No. 0655627 discloses a fast-disintegrating tablet which comprises saccharide and amorphous saccharide, and is manufactured by humidifying and drying after tableting. According to the examples of the above patent, a formed tablet was placed in a 35° C., 85% RH thermohygrostat for 20 minutes and then dried in a 50° C. oven for several tens of minutes; or was placed in a 25° C., 70-80% RH thermohygrostat for 12-24 hours and then dried at 25 to 40° C. for several hours. Consequently, this method is difficult to apply to drugs unstable to moisture and requires cumbersome processes after tableting.

Therefore, there has been a continuous need to develop a fast-disintegrating tablet having fast disintegrability as well as high hardness which can be manufactured without modifying the tableting machine or forming machine conventionally used in a pharmaceutical manufacturing process and without using additional equipment; and a process for manufacturing the same not requiring cumbersome post-treatment processes under harsh conditions after the tableting or forming step.

DISCLOSURE OF INVENTION

Technical Problem

The object of the present invention is to provide a fast-disintegrating tablet having high hardness and fast disintegrability which can be manufactured by employing a tableting machine or forming machine conventionally used in a pharmaceutical manufacturing process; and a process for manufacturing the same not requiring cumbersome post-treatment processes under harsh conditions after the tableting or forming step. Another object of the present invention is to provide slightly wetted granules for manufacturing said fast-disintegrating tablet and a process for manufacturing the same.

Solution to Problem

In order to solve the technical problems, the present invention provides slightly wetted granules comprising a spray-dried mannitol and a sucrose binder.

According to another aspect of the present invention, a process for manufacturing slightly wetted granules which comprise the steps of forming a mixture comprising a spray-dried mannitol and a sucrose binder; and drying said mixture is provided.

According to still another aspect of the present invention, a fast-disintegrating tablet comprising said slightly wetted granules is provided.

According to still another aspect of the present invention, a process for manufacturing a fast-disintegrating tablet which comprises the steps of forming a post-granulation mixture for tableting comprising said slightly wetted granules; compressing said post-granulation mixture to obtain a tablet; and drying said tablet is provided.

Advantageous Effects of Invention

The slightly wetted granules according to the present invention may be manufactured by a wet-granulation method conventionally used in a pharmaceutical manufacturing process. When a fast-disintegrating tablet is manufactured by using the slightly wetted granules, a tableting machine or forming machine generally used in a pharmaceutical manufacturing process may be used; the cumbersome post-treatment processes under harsh conditions after the tableting or forming step may not be needed; and a fast-disintegrating tablet having high hardness and fast disintegrability can be produced—thus, the production cost is low; additional investment in equipment need not be made; packaging, transport and storage are easy; and patients can easily take their medicine.

Mode for the Invention

Unless specified otherwise, the terms and expressions used herein are defined as follows:

The term "loss-on-drying" stated herein refers to an evaporated amount of water, solvent and volatile materials in a sample, expressed as a percentage (%) based on the weight before drying when the sample is dried under heating condition. An exemplary measuring method is as follows: about 2 g or more of sample is taken and evenly spread onto an aluminum plate, and the weight of the sample ("weight after drying") is measured at 105° C. for several to several tens of minutes until there is no change in the value by using an MA100 LOD meter (Sartorius). The loss-on-drying (%) is calculated as follows: after subtracting the weight after drying from the weight before drying, the difference is divided by the weight before drying, and then multiplying by 100. For example, when 2.00 g of sample is taken and 1.95 g is left after the solvent or moisture was evaporated by drying, the loss-on-drying is 2.5%. For accuracy, after one measurement, the next measurement is conducted after a sample inlet is cooled below 35° C., and the three measurements are performed and their average value is determined as the loss-on-drying.

The term "sufficiently dried granules" stated herein refers to granules which are obtained by drying after the wet-granulation step and its loss-on-drying is in an unchanged state even after additional drying. For example, it refers to granules wherein the loss-on-drying of the granules after agglomeration by using a binder solution in a wet-granulation step and drying in a 50° C. convection oven for 4 hours, is equivalent to that of the granules additionally dried for 2 hours in the same way. More specifically, for example, it refers to granules wherein the loss-on-drying values of the following two granules are the same: granules prepared by a process comprising the steps of passing 500 g of the wetted mass agglomerated by using a binder solution in a wet-granulation step through a 30-mesh sieve; drying in a 50° C. convection oven (FO600M, Jeio-Tech) for 2 hours after evenly spreading onto a stainless-steel plate to be about 0.1-2 cm thick; passing by the dried resultant through a 30-mesh sieve; drying for 2 hours again (total drying time is 4 hours); and sieving the dried resultant again with a 30-mesh sieve; and granules additionally dried for 2 hours in the same way as before. The term "the same loss-on-drying value" means that the difference in the loss-on-drying value is within ±0.3%, preferably ±0.2% in light of measurement error. For instance, the loss-on-drying value of the sufficiently dried granules is usually within 3% or 2%, but depending on materials comprised in the granule, it may be within 1% or 0.5%.

The term "slightly wetted granules" stated herein refers to granules having 1.05- to 5-times, preferably 1.1- to 3-times, and most preferably 1.2- to 2.5-times greater loss-on-drying value than that of the sufficiently dried granules, when measuring the loss-on-drying of the granules obtained by a wet-granulation and drying process.

The slightly wetted granules show property having no problem in manufacturing a tablet with a conventionally used amount of a commonly used lubricant by a general tablet-manufacturing process.

The phrase "general tablet-manufacturing process" refers to a process which utilizes a tableting machine or forming machine generally used in pharmaceutics, and employs general humidity and temperature conditions inside a tableting room.

The term "general tableting machine and forming machine" may be a single-punch or multiple-punch tableting machine and refers to machines in which no special modifications are made, such as preventing a tablet from sticking to a punch when tableting by using a special film; or spraying a lubricant into the mold.

The phrase "general humidity and temperature conditions inside a tableting room" refers to within the conventionally controlled humidity and temperature range of the inner-space air where the tableting machine or forming machine is placed—for example, the conditions of 20-30° C. of temperature and 40% or less RH of humidity.

The phrase "conventionally used lubricant" refers to a lubricant that is conventionally used for forming tablets, and any suitable agent may be employed.

The phrase "a conventionally used amount of lubricant" refers to not using excessive lubricant, which means the amount employed in conventional tablet manufacturing—i.e., 3% or less (based on tablet weight), preferably 2% or less, and more preferably 1.5% or less.

The phrase "has no problem in forming a tablet" means that there are no troubles in tableting—for example, during the tableting or forming process, a part or all of the tablet sticks to a punch or mold, or is crushed; or when taking the produced tablet in a container or transferring it to another container, a part or all of the tablet is crushed. In addition, it means that a mixture for tableting has sufficient flowability to produce tablets without variations in weight.

Hereinafter, the present invention will be described in more detail.

Slightly Wetted Granules

The slightly wetted granules of the present invention comprise a spray-dried mannitol and a sucrose binder.

According to one embodiment of the present invention, the slightly wetted granules may further comprise an active ingredient and/or various additional components other than the spray-dried mannitol and the sucrose binder for the purpose—such as effectiveness in granule manufacturing, stability of active ingredients, appearance, color, protection, binding, performance improvement, manufacturing process improvement, etc.

Mannitol dissolves well in water (1 part per 5.5 parts of water at 20° C.); is chemically stable and non-hygroscopic; does not undergo the Maillard reaction with amino group; and has a good taste when it disintegrates in the oral cavity.

Spray-dried mannitol has advantages other than the above properties, such as fast disintegration in water due to its porosity; good flowability; and good compressibility. Examples of such spray-dried mannitol include commercially available Mannogen™ EZ (SPI Pharma), Pearlitol® SD (Roquette), etc., but are not limited thereto. Spray-dried mannitol has various applications in the pharmaceutical art due to said properties and is mainly used as a diluent in direct tableting without manufacturing granules. Unconventionally, the present invention uses spray-dried mannitol for wet granulation, thereby making the granules have more micropores than when mannitol powder is used for wet granulation; confers enhanced compressibility and flowability, which make tablets disintegrate faster and have better hardness and friability.

Preferably, the slightly wetted granules of the present invention may comprise the spray-dried mannitol in an amount of 20 to 98% by weight, more preferably 30 to 95% by weight, and even more preferably 50 to 90% by weight based on total weight of the slightly wetted granules. If the amount of spray-dried mannitol is less than 20% by weight or greater than 98% by weight based on total weight of the slightly wetted granules, tablet hardness may be lowered or disintegration time may be prolonged.

Preferably, the sucrose binder may be used by dissolving it in water, non-aqueous solvent or a mixed solvent thereof, more preferably a mixed solvent of water and ethanol. The concentration of sucrose may be 1 to 60% (w/w), preferably 5 to 50% (w/w) based on such solvents.

Preferably, the slightly wetted granules of the present invention may comprise the sucrose binder in a dried amount of 1 to 50 parts by weight, more preferably 2 to 30 parts by weight, and even more preferably 3 to 15 parts by weight based on 100 parts by weight of said spray-dried mannitol. If the amount of dried sucrose binder is less than 1 part by weight based on 100 parts by weight of the spray-dried mannitol, the tablet hardness may be lowered, and if it is greater than 50 parts by weight, the disintegration time may be prolonged.

The slightly wetted granules of the present invention may or may not comprise an active ingredient. If the slightly wetted granules comprises an active ingredient, it may be mixed in a solid state with the spray-dried mannitol before adding a binder solution for wet granulation, and its state may be a powdered state; crystalline state; granular state; fine-powdered state; or nanoparticle state. Alternatively, the active ingredient may be dissolved or dispersed in a solvent when the sucrose binder solution is prepared.

The slightly wetted granules of the present invention may further comprise additional ingredients for manufacturing said granule. Exemplary additional ingredients for manufacture of the granule include dry binder, coloring agent, flavor, sweetening agent, stabilizing agent, antioxidant, etc., which may be added in a solid state along with the spray-dried mannitol.

Preferably, the slightly wetted granules of the present invention may comprise the dry binder among the above additional ingredients for manufacture of the granule in an amount of 50 parts by weight or less (e.g., 0.1 to 50 parts by weight), more preferably 30 parts by weight or less, and even more preferably 15 parts by weight or less based on 100 parts by weight of the spray-dried mannitol.

The dry binder may be saccharide, sugar alcohol, starch, polysaccharide, cellulose derivative, or a mixture thereof—for example, one or more selected from: fructose, lactitol, lactose, maltitol, maltose, mannitol, sorbitol, sucrose, erythritol, xylitol, maltodextrin, isomalt, dextrin, dextrose, dextrate, starch, microcrystalline cellulose, silicified microcrystalline cellulose, powdered cellulose, cellulose acetate, STARLAC® (a spray-dried solid powder consisting of 15% corn starch and 85% α-lactose monohydrate, Roquette American Inc.), MICROCELAC® (a spray-dried solid powder consisting of 75% α-lactose monohydrate and 25% microcrystalline cellulose, Meggle Excipients & Technology), CELLACTOSE® (a spray-dried compound consisting of 75% α-lactose monohydrate and 25% cellulose powder, Meggle Excipients & Technology), etc., but are not limited thereto.

Other ingredients except for the dry binder among the additional ingredients for manufacture of the granule—i.e. coloring agent, flavor, sweetening agent, stabilizing agent, antioxidant, etc.—may be dissolved or dispersed during the preparation of the sucrose binder solution.

Process for Manufacturing the Slightly Wetted Granules

The slightly wetted granules of the present invention as mentioned above may be manufactured by a method comprising the steps of: forming granules comprising a spray-dried mannitol and a sucrose binder; drying said granules to prepare slightly wetted granules having 1.05- to 5-times greater loss-on-drying value than the sufficiently dried granules.

Preferably, the sucrose binder dissolved in water, non-aqueous solvent or mixed solvent thereof may be used in preparing a mixture for the formation of the granule comprising the spray-dried mannitol and the sucrose binder.

The granule comprising the spray-dried mannitol and the sucrose binder may further comprise an active ingredient and/or additional ingredients for the manufacture of the granule. The way to introduce them into said mixture is described above.

The slightly wetted granules of the present invention may be manufactured by the wet-granulation process conventionally used in the pharmaceutical art. According to one embodiment of the present invention, a mixture comprising a spray-dried mannitol; a sucrose binder; optional active ingredient; and/or optional additional ingredient for the manufacture of the granule may be prepared in a state of agglomerated particle mass by using a granulator, a mixer, a U-type mixer, a high-speed mixer, a fluidized bed granulator, etc., or manually The prepared agglomerated particle mass may directly undergo a drying step or may undergo a drying step after sieving. According to one embodiment of the present invention, the agglomerated particle mass may be granulated by passing through a 30-mesh sieve.

Conventional drying techniques—for example, convection-oven drying, vacuum-oven drying, drying by fluidized bed dryer, drying by dryer, natural drying at room temperature, etc.—may be used to prepare the slightly wetted granules. In addition, the slightly wetted granules of desired size may be obtained by additional sieving during or after drying.

Fast-Disintegrating Tablet

The fast-disintegrating tablet of the present invention comprises said slightly wetted granules.

Preferably, the fast-disintegrating tablet of the present invention may comprise the slightly wetted granules in an amount of 50 to 99% by weight, more preferably 60 to 98% by weight and even more preferably 70 to 97% by weight based on total weight of the tablet. If the amount of slightly wetted granules is less than 50% by weight based on total weight of the tablet, the tablet may not exhibit the properties of the fast-disintegrating tablet—i.e., high hardness and fast disintegrability; and if greater than 99% by weight, troubles in tableting may occur or disintegration in water may be poor.

The fast-disintegrating tablet of the present invention may further comprise an active ingredient and/or additional ingredients for the manufacture of tablet other than the spray-dried mannitol and the sucrose binder comprised in the slightly wetted granules. Such an active ingredient and/or additional ingredients for the manufacture of tablet may be introduced to the slightly wetted granules, or alternatively, during the formation of post-granulation mixture for tableting. The active ingredient introduced during the preparation step of post-granulation mixture may be in a powdered state, a crystalline state, a granular state, a fine-powdered state, a nanoparticular state, the state of taste-masked particle or sustained-release coated particle for delivery control, etc. Additional ingredients for the manufacture of tablet may be introduced to achieve additional objects—such as improving efficiency of tableting; prompting disintegration; stabilizing active ingredient; improving appearance, color, protection, binding and performance; improving manufacturing process; and the like. Examples of the additional ingredients for the manufacture of tablet include a disintegrating agent, a lubricant, surfactant, a dry binder, a coloring agent, a flavor, a sweetening agent, a stabilizing agent, an antioxidant, a souring agent, etc., but they are not limited thereto.

The specific type and usage of the above additional ingredients and the way to introduce such ingredients into the tablet of the present invention would be well known to a person having ordinary skill in the art, and can variously be modified.

Specifically, the disintegrating agent may be one or more selected from the group consisting of sodium starch glycolate, crospovidone, low-substituted hydroxypropyl cellulose, cross-linked sodium carboxymethyl cellulose, starch and the like. The amount of disintegrating agent may suitably be 7% by weight or less, preferably 5% by weight or less, and more preferably 3% by weight or less, based on total weight of the tablet.

Specifically, the lubricant may be one or more selected from the group consisting of stearic acid, glyceryl behenate, glyceryl monostearate, magnesium stearate, calcium stearate, silicon dioxide, talc, sugar ester, sodium stearyl fumarate, magnesium silicate, sodium stearate, poly(ethylene glycol), polyoxypropylene-polyoxyethylene block copolymer, colloidal silicon dioxide and sucrose esters of fatty acids. The amount of lubricant may suitably be 3% by weight or less, preferably 2% by weight or less, and more preferably 1.5% by weight or less, based on total weight of the tablet.

Preferably, the fast-disintegrating tablet has one or more, more preferably two or more, even more preferably three or more, and most preferably all of the following four properties:

Hardness: 2.5 Kp or more (for example, 2.5 to 20 Kp), preferably 3.0 Kp or more, and more preferably 4.0 Kp or more Friability: 1.0% or less (for example, 0.001 to 1.0%), preferably 0.8% or less, and more preferably 0.5% or less Disintegration time in water: 2 minutes or less (for example, 1 second to 1 minute), preferably 1 minute or less, and more preferably 40 seconds or less Disintegration time in oral cavity: 40 seconds or less (for example, 1 second to 40 seconds), preferably 30 seconds or less, and more preferably 25 seconds or less.

Method for Manufacturing the Fast-Disintegrating Tablet

The fast-disintegrating tablet of the present invention as described above may be manufactured by a method comprising the steps of: forming a post-granulation mixture for tableting comprising said slightly wetted granules; compressing said mixture to obtain a tablet; and drying said tablet.

The fast-disintegrating tablet may be manufactured by using a tableting machine or forming machine conventionally used in the pharmaceutical art. In addition, a low-pressure compressing process may be used for tableting, and tablet may be dried under a mild condition.

The compressing pressure in the step of compressing post-granulation mixture for tableting comprising the slightly wetted granules to obtain a tablet is generally low—that is, about 150 MPa or less (for example, from 1 Pa to 150 MPa), preferably about 35 MPa or less and more preferably about 10 MPa or less.

In order for the tablet to disintegrate quickly in the oral cavity, water has to be rapidly absorbed into the inner core thereof and the ingredients also need to dissolve quickly. Therefore, it is important for the compressed tablet to maintain high porosity. The low-pressure tableting process is usually employed to maintain high porosity of the compressed tablet; but if the tablet is processed under low pressure, its hardness and friability cannot but be worsen. However, by using the slightly wetted granules of the present invention, the tablet can be produced even by low-pressure tableting without any such troubles in tableting; and after the drying step, the tablet has not only good physical properties of high hardness and low friability but also fast disintegrability.

The mild condition for drying tablet may be conditions of room temperature and humidity which is not too high—for example, 20 to 30° C. of temperature and 40% RH or less of humidity. In order to dry faster and completely, a 20 to 50° C. low-temperature convection oven may be used; and a method of providing dry air, a method using a dehumidifier, a method using a dehumidifying agent, etc. may be used.

Active Ingredient

The active ingredient may be mixed into a solid in the process of manufacturing the slightly wetted granules; added during the preparation of the sucrose binder solution; or introduced in the step of forming post-granulation mixture. Such an active ingredient may be in a solution state, paste state, powder state, crystalline state, granular state, fine-powdered state, nanoparticular state, state of taste-masked particle or sustained-release coated particle for delivery control, etc.

In addition, the active ingredient may be used alone, or two or more active ingredients may be used as a combined formulation.

Active ingredients useful in the present invention are too many to mention one by one herein. Representative examples of the drug which can be formulated as the fast-disintegrating tablet of the present invention include the following, but are not limited to:

anti-migraine drugs, such as almotriptan, ergotamine tatrate, frovatriptan, methysergide maleate, sumatriptan succinate, zolmitriptan, etc.;

ADHD (Attention Deficit Hyperactivity Disorder) drugs, such as methylphenidate, atomoxetine, etc.;

erectile dysfunction drugs, such as sildenafil, vardenafil, alprostadil, tadalafil, mirodenafil, udenafil, etc.;

anti-rheumatic drugs, such as auranofin, azathioprine, cyclosporine, hydroxy-chloroquine sulfate, lefunomide, methotrexate, penicillamine, sulfasalazine, etc.;

nonsteroidal anti-inflammatory drugs, such as acetaminophen, aspirin, diclofenac, etodolac, fenoprofen, ibuprofen, ketoprofen, naproxen, indomethacin, ketorolac, sulindac, tolmetin, meclofenamate, mefenamic acid, nabumetone, meloxicam, piroxicam, celecoxib, rofecoxib, etc.;

opioids, such as buprenorphine, codeine, fentanyl, hydrocodone, hydromorphone, levorphanol, meperidine, morphine, oxycodone, pentazocine, propoxyphene, tramadol, etc.;

anti-mycobacterial drugs, such as aminosalicylic acid salts, clofazimine, cycloserine, ethionamide, rifabutin, etc.;

anti-parasitic drugs, such as albendazol, ivermectin, mebendazol, praziquantel, etc.;

anti-viral drugs, such as valacyclovir, didanosine, famciclovir, valganciclovir, indinavir, lamivudine, nelfinavir mesylate, nevirapine, ritonavir, stavudine, oseltamivir phosphate, etc.;

beta-lactam, such as amoxicillin, amoxicillin and potassium clavulanate, ampicillin, cefuroxime sodium, cefuroxime axetil, penicillin G and Y salts, cefditoren, cefixime, cloxacillin sodium, dicloxacillin sodium, etc.;

macrolide antibiotics, such as erythromycin estolate, erythromycin ethylsuccinate, erythromycin stearate, etc.;

fluoroquinolones, such as ciprofloxacin, enoxacin, etc.;

tetracyclines, such as demeclocycline hydrochloride, doxycycline calcium, tetracycline, tetracycline hydrochloride, etc.;

alkylating agents, such as altretamine, busulfan, chlorambucil, melphalan, cyclophosphamide, procarbazine hydrochloride, temozolomide, etc.;

antimetabolites, such as methotrexate, mercaptopurine, thioguanine, etc.;

hormonal drugs and antagonists, such as bicalutamide, flutamide, nirutamide, aminoglutethimide, anastrozole, exemestane, letrozole, tamoxifen citrate, toremifene citrate, etc.;

mitotic inhibitors, such as etoposide phosphate, etc.;

immunosuppressive drugs, azathioprine, cyclosporine, mycophenolate mofetil, sirolimus, tacrolimus, etc.;

antiarrhythmics drugs, such as amiodarone hydrochloride, digoxin, disopyramide phosphate, dofetilide, flecainide acetate, mexiletine hydrochloride, moricizine hydrochloride, procainamide hydrochloride, propafenone hydrochloride, quinidine sulfate, quinidine gluconate, sotalol hydrochloride, tocainide, etc.;

antihypertensive drugs, such as doxazosin mesylate, prazosin hydrochloride, terazosin hydrochloride, benazepril, captopril, clonidine hydrochloride, enalapril, hydralazine hydrochloride, labetalol hydrochloride, losartan potassium, methyldopate hydrochloride, minoxidil, moexipril, trandolapril, candesartan, irbesartan, losartan, telmisartan, valsartan, guanabenz acetate, guanadrel sulfate, guanfacine hydrochloride, reserpine, etc.;

beta-adrenergic blocking drugs, such as acebutolol, atenolol, betaxolol, bisoprolol, carteolol, carvedilol, labetalol, metoprolol, nadolol, penbutolol, pindolol, propranolol, sotalol, timolol, etc.;

calcium channel blockers, such as amlodipine, bepridil, diltiazem, felodipine, isradipine, nicardipine, nifedipine, nimodipine, nisoldipine, verapamil, etc.;

lipid-lowering drugs, such as fenofibrate, gemfibrozil, niacin, atorvastatin, fluvastatin, lovastatin, pravastatin, simvastatin, etc.;

nitrates, such as isosorbide dinitrate, nitroglycerin, nitroprusside sodium, etc.;

antiseizure drugs, such as carbamazepine, clonazepam, ethosuximide, felbamate, gabapentin, lamotrigine, levetiracetam, oxcarbazepine, phenobarbital, phenytoin, primidone, tiagabine, topiramate, valproic acid, divalproex sodium, zonisamide, etc.;

antidepressants, such as mirtazapine, bupropion, amoxapine, phenelzine, tranylcypromine, citalopram, fluoxetine, fluvoxamine, paroxetine, sertraline, venlafaxine, maprotiline, trazodone, nefazodone, amitriptyline, clomipramine, desipramine, doxepin, imipramine, nortriptyline, protriptyline, trimipramine, etc.;

antipsychotic drugs, such as chlorpromazine, thioridazine, loxapine, molindone, clozapine, olanzapine, quetiapine, risperidone, ziprasidone, fluphenazine, haloperidol, perphenazine, trifluoperazine, thiothixene, paliperidone, etc.;

anxiolytics, sedatives and hypnotics, such as alprazolam, lorazepam, oxazepam, chlordiazepoxide, clorazepate, diazepam, halazepam, midazolam, triazolam, zaleplon, zolpidem, estazolam, temazepam, flurazepam, quazepam, meprobamate, phenobarbital, chloral hydrate, ethchlorvynol, glutethimide, pentobarbital, secobarbital, etc.;

neurodegenerative disease drugs, such as amantadine, benztropine mesylate, carbidopa and levodopa, donepezil, bromocriptine, pergolid, pramipexole, ropinirole, etc.;

anti-glaucoma drugs, such as acetazolamide, dichlorphenamide, methazolamide, etc.;

acid-peptic disease drugs, such as aluminum carbonate, aluminum hydroxide, magnesium hydroxide, sodium bicarbonate, calcium carbonate, magaldrate, bismuth salts, cimetidine, famotidine, nizatidine, ranitidine, misoprostol, lansoprazole, omeprazole, pantoprazole, rabeprazole, sucralfate, etc.;

antiemetics, such as buclizine, cyclizine, dimenhydrinate, diphenhydramine, meclizine, dronabinol, chlorpromazine, perphenazine, prochlorperazine, promethazine, thiethylperazine, triflupromazine, dolasetron, granisetron, ondansetron, dexamethasone, lorazepam, granisetron, ramosetron, aprepitant, etc.;

gastrointestinal motility drugs, such as bisacodyl, diphenoxylate hydrochloride and atropine sulfate, docusate salts, loperamide, magnesium salts, metoclopramide, ursodiol, etc.;

coagulants and anticoagulants, such as clopidogrel bisulfate, phytonadione, ticlopidine, warfarin sodium, etc.;

hematopoiesis stimulants, such as iron salts, etc.;

adrenal hormones, such as cortisone, hydrocortisone, methylprednisolone, prednisone, triamcinolone, betamethasone, dexamethasone, fludrocortisone, etc.;

anti-diabetic drugs, such as acarbose, metformin, nateglinide, repaglinide, acetohexamide, chlorpropamide, tolazamide, tolbutamide, glimepiride, glipizide, glyburide, pioglitazone, rosiglitazone, etc.;

contraceptives, such as norethindrone, norgestrel, levonorgestrel, etc.;

female sex hormones, such as estradiol and esters thereof, estrogen, estropipate, medroxyprogesterone, mifepristone, norethindrone acetate, progesterone, raloxifene, etc.;

thyroid and anti-thyroid hormones, such as iodide, levothyroxine sodium, liothyronine sodium, liotrix, methimazole, propylthiouracil, etc.;

diuretics, such as amyloid hydrochloride, bumetanide, ethacrynic acid, furosemide, torasemide, hydrochlorothiazide, chlorthiazide, chlorthalidone, indapamide, metolazone, polythiazide, quinthazone, trichomethiazide, spironolactone, triamterene, etc.;

electrolytes, such as chelated magnesium, magnesium chloride, magnesium hydroxide, magnesium oxide, potassium salts, etc.;

gout drugs, such as allopurinol, colchicine, probenecid, sulfinpyrazone, etc.;

asthma drugs, such as albuterol sulfate, montelukast sodium, theophylline, zileuton, etc.;

antihistamines, such as acrivastine, azatadine, brompheniramine maleate, carbinoxamine maleate, cetirizine hydrochloride, chlorpheniramine maleate, diphenhydramine hydrochloride, clemastine fumarate, cyproheptadine hydrochloride, fexofenadine, hydroxyzine, loratidine, desloratadine, etc.;

drugs for cough and cold, such as dextromethorhpan hydrobromide, guaifenesin, pseudoephedrine hydrochloride, etc.; and health functional foods.

The following examples illustrate the present invention and are not intended as a means of defining the limits and scope of the present invention.

EXAMPLES

The following methods were used for analyzing properties of the Examples and Comparative Examples:

Hardness Measurement

The tablet hardness was measured by using a hardness tester 8M (Dr. Schleuniger, Switzerland). At least 6 specimens were measured, and their average values were recorded.

Friability Measurement

The friability test method was performed according to the method described in the Tablet Friability of the General Chapters of USP (US Pharmacopoeia) 25 describing general tests and assays.

Disintegration Test in Water

The disintegration test was performed according to a disintegration test method among general test methods described in the 8th edition of the Korean Pharmacopoeia. Water was used as test liquid, 6 specimens were subjected to the test at 37° C., and their average values were recorded.

Disintegration Test in the Oral Cavity

For a fast-disintegrating tablet, disintegration tests were performed in the oral cavity with applicants. Applicants were randomly selected and had their mouths washed out with water. Disintegration time began by measuring with a stopwatch which was started immediately after the tablet was placed on the tongue. The applicants were permitted to move the fast-disintegrating tablet to the roof of mouth using their tongue; roll it gently without biting the tablet; and roll it from side to side. The stopwatch was stopped right after the tablet could be swallowed with saliva as it was disintegrated, and the time was recorded.

Loss-on-Drying Value

For loss-on-drying value of powder, granule, etc., about 2 g of sample was taken and evenly spread onto an aluminum plate, and the loss-on-drying was measured for several to several tens of minutes by using an MA100 LOD meter (Sartorius). When there was no change in value, the test was set to be automatically over.

For loss-on-drying value of tablet, a sample corresponding to about 2 g was taken and placed on an aluminum plate, and its loss-on-drying was measured with the same method as for powder or granule.

For loss-on-drying value of crushed tablet, a tablet corresponding to about 2 g was taken and then crushed in a mortar. Its loss-on-drying was then measured with the same method as for powder or granule.

Example 1

Use of Spray-Dried Mannitol and 50% Sucrose Solution 318.4 g of spray-dried mannitol (Mannogem™ EZ, SPI) was added to a 3 L high-speed mixer, and 58.1 g of 50% (w/w) sucrose (Samyang Corporation) solution (ethanol:water=4:6 (w:w)) was added thereto and kneaded with rotational mixing at an impeller speed of 150 rpm and a chopper speed of 1,700 rpm. After removal, the product was granulated by passing through a 30-mesh sieve (mesh size: 600 μm) and dried in a 50° C. oven for about 50 minutes. Drying time was appropriately controlled such that the loss-on-drying value of the final slightly wetted granules was about 1.0%. The final loss-on-drying value of the slightly wetted granules was 0.96%.

324.7 g of the manufactured slightly wetted granules, 10.2 g of low-substituted hydroxypropyl cellulose (L-HPC), 3.4 g of calcium stearate and 1.7 g of stearic acid were admixed, and then tableted by a single-punch tablet press (EK-0, Korsch) such that the fast-disintegrating tablet was 8.5 mm in diameter and weighed 170 mg. Immediately after tableting, tablet hardness was about 2.1 Kp. After completion of tableting, the product was held at room temperature (about 25° C., 10-30% RH) for 2 days and then packaged. Physical properties of the packaged tablet were as follows: hardness, 4.6 Kp; friability, 0.34%; disintegration time in water, 26.5 seconds; disintegration time in the oral cavity, 12 seconds; loss-on-drying value of the tablet, 0.42%; loss-on-drying value of the crushed tablet, 0.68%.

Example 2

Use of Spray-Dried Mannitol, Dry Binder (StarLac) and 50% Sucrose Solution 302.5 g of spray-dried mannitol (Mannogem™ EZ, SPI) and 15.9 g of spray-dried solid powder consisting of 15% corn starch and 85% α-lactose monohydrate (StarLac, Roquette) as a dry binder were added to a 3 L high-speed mixer, and 58.1 g of 50% (w/w) sucrose (Samyang Corporation) solution (ethanol:water=4:6 (w:w)) was added thereto and kneaded with rotational mixing at an impeller speed of 150 rpm and a chopper speed of 1,700 rpm. After removal, the product was granulated by passing through a 30-mesh sieve (mesh size: 600 μm) and dried in a 50° C. oven for about 50 minutes. Drying time was appropriately controlled such that the loss-on-drying value of the final slightly wetted granules was about 1.0%. The final loss-on-drying value of the slightly wetted granules was 1.12%.

324.7 g of the manufactured slightly wetted granules, 10.2 g of low-substituted hydroxypropyl cellulose (L-HPC), 3.4 g of calcium stearate and 1.7 g of stearic acid were admixed, and then tableted by a single-punch tablet press (EK-0, Korsch) such that the fast-disintegrating tablet was 8.5 mm in diameter and weighed 170 mg. Immediately after tableting, tablet hardness was about 2.1 Kp. After completion of tableting, the product was held at room temperature (about 25° C., 10-30% RH) for 2 days and then packaged. Physical properties of the packaged tablet were as follows: hardness, 4.0 Kp; friability, 0.45%; disintegration time in water, 30 seconds; disintegration time in the oral cavity, 15 seconds; loss-on-drying value of the tablet, 0.47%; loss-on-drying value of the crushed tablet, 0.8%.

Example 3

Use of Spray-Dried Mannitol, Dry Binder (Lactose) and 50% Sucrose Solution 302.5 g of spray-dried mannitol (Mannogem™ EZ, SPI) and 15.9 g of lactose (Pharmatose 200M, DMV) as a dry binder were added to a 3 L high-speed mixer, and 58.1 g of 50% (w/w) sucrose (Samyang Corporation) solution (ethanol:water=4:6 (w:w)) was added thereto and kneaded with rotational mixing at an impeller speed of 150 rpm and a chopper speed of 1,700 rpm. After removal, the product was granulated by passing through a 30-mesh sieve (mesh size: 600 μm) and dried in a 50° C. oven for about 50 minutes. Drying time was appropriately controlled such that the loss-on-drying value of the final slightly wetted granules was about 1.0%. The final loss-on-drying value of the slightly wetted granules was 0.86%.

324.7 g of the manufactured slightly wetted granules, 10.2 g of low-substituted hydroxypropyl cellulose (L-HPC), 3.4 g of calcium stearate and 1.7 g of stearic acid were admixed, and then tableted by a single-punch tablet press (EK-0, Korsch) such that the fast-disintegrating tablet was 8.5 mm in diameter and weighed 170 mg of weight. Immediately after tableting, tablet hardness was about 2.0 Kp. After completion of tableting, the product was held at room temperature (about 25° C., 10-30% RH) for 2 days and then packaged. Physical properties of the packaged tablet were as follows: hardness, 4.7 Kp; friability, 0.4%; disintegration time in water, 17 seconds; disintegration time in the oral cavity, 10 seconds; loss-on-drying value of the tablet, 0.33%; loss-on-drying value of the crushed tablet, 0.61%.

Example 4

Use of Spray-Dried Mannitol, Dry Binder (Lactose) and 40% Sucrose Solution 311 g of spray-dried mannitol (Mannogem™ EZ, SPI) and 16.3 g of lactose (Pharmatose 200M, DMV) as a dry binder were added to a 3 L high-speed mixer, and 58.1 g of 40% (w/w) sucrose (Samyang Corporation) solution (ethanol:water=4:6 (w:w)) was added thereto and kneaded with rotational mixing at an impeller speed of 150 rpm and a chopper speed of 1,700 rpm. After removal, the product was granulated by passing through a 30-mesh sieve (mesh size: 600 μm) and dried in a 50° C. oven for about 50 minutes. Drying time was appropriately controlled such that the loss-on-drying value of the final slightly wetted granules was about 1.0%. The final loss-on-drying value of the slightly wetted granules was 0.98%.

324.7 g of the manufactured slightly wetted granules, 10.2 g of low-substituted hydroxypropyl cellulose (L-HPC), 3.4 g of calcium stearate and 1.7 g of stearic acid were admixed and then tableted by a single-punch tablet press (EK-0, Korsch) such that the fast-disintegrating tablet was 8.5 mm in diameter and weighed 170 mg. Immediately after tableting, tablet hardness was about 2.0 Kp. After completion of tableting, the product was held at room temperature (about 25° C., 10-30% RH) for 2 days and then packaged. Physical properties of the packaged tablet were as follows: hardness, 5.7 Kp; friability, 0.3%; disintegration time in water, 25 seconds; disintegration time in the oral cavity, 14 seconds; loss-on-drying value of the tablet, 0.37%; loss-on-drying value of the crushed tablet, 0.49%.

Example 5

Use of Spray-Dried Mannitol, Dry Binder (Lactose) and 30% Sucrose Solution 311 g of spray-dried mannitol (Mannogem™ EZ, SPI) and 16.3 g of lactose (Pharmatose 200M, DMV) as a dry binder were added to a 3 L high-speed mixer, and 58.1 g of 30% (w/w) sucrose (Samyang Corporation) solution (ethanol:water=4:6 (w:w)) was added thereto and kneaded with rotational mixing at an impeller speed of 150 rpm and a chopper speed of 1,700 rpm. After removal, the product was granulated by passing through a 30-mesh sieve (mesh size: 600 μm) and dried in a 50° C. oven for about 50 minutes. Drying time was appropriately controlled such that the loss-on-drying value of the final slightly wetted granules was about 1.0%. The final loss-on-drying value of the slightly wetted granules was 1.08%.

324.7 g of the manufactured slightly wetted granules, 10.2 g of low-substituted hydroxypropyl cellulose (L-HPC), 3.4 g of calcium stearate and 1.7 g of stearic acid were admixed and then tableted by a single-punch tablet press (EK-0, Korsch) such that the fast-disintegrating tablet was 8.5 mm in diameter and weighed 170 mg. Immediately after tableting, tablet hardness was about 1.1 Kp. After completion of tableting, the product was held at room temperature (about 25° C., 10-30% RH) for 2 days and then packaged. Physical properties of the packaged tablet were as follows: hardness, 5.2 Kp; friability, 0.48%; disintegration time in water, 14 seconds; disintegration time in the oral cavity, 7 seconds; loss-on-drying value of the tablet, 0.43%; loss-on-drying value of the crushed tablet, 0.49%.

Example 6

Use of Spray-Dried Mannitol, Dry Binder (Lactose) and 20% Sucrose Solution 311 g of spray-dried mannitol (Mannogem™ EZ, SPI) and 16.3 g of lactose (Pharmatose 200M, DMV) as a dry binder were added to a 3 L high-speed mixer, and 58.1 g of 20% (w/w) sucrose (Samyang Corporation) solution (ethanol:water=4:6 (w:w)) was added thereto and kneaded with rotational mixing at an impeller speed of 150 rpm and a chopper speed of 1,700 rpm. After removal, the product was granulated by passing through a 30-mesh sieve (mesh size: 600 μm) and dried in a 50° C. oven for about 50 minutes. Drying time was appropriately controlled such that the loss-on-drying value of the final slightly wetted granules was about 1.0%. The final loss-on-drying value of the slightly wetted granules was 1.06%.

324.7 g of the manufactured slightly wetted granules, 10.2 g of low-substituted hydroxypropyl cellulose (L-HPC), 3.4 g of calcium stearate and 1.7 g of stearic acid were admixed and then tableted by a single-punch tablet press (EK-0, Korsch) such that the fast-disintegrating tablet was 8.5 mm in diameter and weighed 170 mg. Immediately after tableting, tablet hardness was about 1.1 Kp. After completion of tableting, the product was held at room temperature (about 25° C., 10 to 30% RH) for 2 days and then packaged. Physical properties of the packaged tablet were as follows: hardness, 4.3 Kp; friability, 0.12%; disintegration time in water, 14 seconds; disintegration time in the oral cavity, 7 seconds; loss-on-drying value of the tablet, 0.72%; loss-on-drying value of the crushed tablet, 1.16%.

Example 7

Use of Spray-Dried Mannitol, Dry Binder (Lactose) and 10% Sucrose Solution 311 g of spray-dried mannitol (Mannogem™ EZ, SPI) and 16.3 g of lactose (Pharmatose 200M, DMV) as a dry binder were added to a 3 L high-speed mixer, and 58.1 g of 10% (w/w) sucrose (Samyang Corporation) solution (ethanol:water=4:6 (w:w)) was added thereto and kneaded with rotational mixing at an impeller speed of 150 rpm and a chopper speed of 1,700 rpm. After removal, the product was granulated by passing through a 30-mesh sieve (mesh size: 600 μm) and dried in a 50° C. oven for about 50 minutes. Drying time was appropriately controlled such that the loss-on-drying value of the final slightly wetted granules awas about 1.0%. The final loss-on-drying value of the slightly wetted granules was 0.91%.

324.7 g of the manufactured slightly wetted granules, 10.2 g of low-substituted hydroxypropyl cellulose (L-HPC), 3.4 g of calcium stearate and 1.7 g of stearic acid were admixed and then tableted by a single-punch tablet press (EK-0, Korsch) such that the fast-disintegrating tablet was 8.5 mm in diameter and weighed 170 mg. Immediately after tableting, tablet hardness was about 1.7 Kp. After completion of tableting, the product was held at room temperature (about 25° C., 10-30% RH) for 2 days and then packaged. Physical properties of the packaged tablet were as follows: hardness, 5.8 Kp; friability, 0.06%; disintegration time in water, 13 seconds; disintegration time in the oral cavity, 7 seconds; loss-on-drying value of the tablet, 0.61%; loss-on-drying value of the crushed tablet, 0.72%.

Example 8

Use of Spray-Dried Mannitol, Dry Binder (Fructose) and 30% Sucrose Solution 302.5 g of spray-dried mannitol (Mannogem™ EZ, SPI) and 15.9 g of fructose (Fructofin, Danisco) as a dry binder were added to a 3 L high-speed mixer, and 58.1 g of 30% (w/w) sucrose (Samyang Corporation) solution (ethanol:water=4:6 (w:w)) was added thereto and kneaded with rotational mixing at an impeller speed of 150 rpm and a chopper speed of 1,700 rpm. After removal, the product was granulated by passing through a 30-mesh sieve (mesh size: 600 μm) and dried in a 50° C. oven for about 50 minutes. Drying time was appropriately controlled such that the loss-on-drying value of the final slightly wetted granules was about 1.5%. The final loss-on-drying value of the slightly wetted granules was 1.49%.

324.7 g of the manufactured slightly wetted granules, 10.2 g of low-substituted hydroxypropyl cellulose (L-HPC), 3.4 g of calcium stearate and 1.7 g of stearic acid were admixed and then tableted by a single-punch tablet press (EK-0, Korsch) such that the fast-disintegrating tablet was 8.5 mm in diameter and weighed 170 mg. Immediately after tableting, tablet hardness was about 1.2 Kp. After completion of tableting, the product was held at room temperature (about 25° C., 10-30% RH) for 2 days and then packaged. Physical properties of the packaged tablet were as follows: hardness, 10.4 Kp; friability, 0.14%; disintegration time in water, 28 seconds; disintegration time in the oral cavity, 30 seconds; loss-on-drying value of the tablet, 0.75%; loss-on-drying value of the crushed tablet, 0.82%.

Comparative Example 1

Use of Mannitol Powder, Dry Binder (Lactose) and 30% Sucrose Solution 311.01 g of mannitol powder (Merck) instead of spray-dried mannitol and 16.31 g of lactose (Pharmatose 200M, DMV) as a dry binder were added to a 3 L high-speed mixer, and 58.1 g of 30% (w/w) sucrose (Samyang Corporation) solution (ethanol:water=4:6 (w:w)) was added thereto and kneaded with rotational mixing at an impeller speed of 150 rpm and a chopper speed of 1,700 rpm. After removal, the product was granulated by passing through a 30-mesh sieve (mesh size: 600 μm) and dried in a 50° C. oven for about 50 minutes. Drying time was appropriately controlled such that the loss-on-drying value of the final slightly wetted granules was about 1.0%. The final loss-on-drying value of the slightly wetted granules was 0.96%.

324.7 g of the manufactured granule, 10.2 g of low-substituted hydroxypropyl cellulose (L-HPC), 3.4 g of calcium stearate and 1.7 g of stearic acid were admixed and then tableted by a single-punch tablet press (EK-0, Korsch) such that the fast-disintegrating tablet was 8.5 mm in diameter and weighed 170 mg. Immediately after tableting, tablet hardness was about 1.2 Kp. After completion of tableting, the product was held at room temperature (about 25° C., 10-30% RH) for 2 days and then packaged. Physical properties of the packaged tablet were as follows: hardness, 1.2 Kp; friability, 2.5%; disintegration time in water, 33 seconds; disintegration time in the oral cavity, 15 seconds; loss-on-drying value of the tablet, 0.37%; loss-on-drying value of the crushed tablet, 0.42%.

Comparative Example 2

Use of Spray-Dried Mannitol, Dry Binder (Fructose) and 30% Sucrose Solution But Use of Sufficiently Dried Granules 302.5 g of spray-dried mannitol (Mannogem™ EZ, SPI) and 15.9 g of fructose (Fructofin, Danisco) as a dry binder were added to a 3 L high-speed mixer, and 58.1 g of 30% (w/w) sucrose (Samyang Corporation) solution (ethanol:water=4:6 (w:w)) was added thereto and kneaded with rotational mixing at an impeller speed of 150 rpm and a chopper speed of 1,700 rpm. After removal, the product was granulated by passing through a 30-mesh sieve (mesh size: 600 μm), dried in a 50° C. oven for 2 hours, and subjected to one more cycle of sieving and drying for 2 hours to obtain sufficiently dried granules. The loss-on-drying value of sufficiently dried granules was 0.87%.

324.7 g of the manufactured granule, 10.2 g of low-substituted hydroxypropyl cellulose (L-HPC), 3.4 g of calcium stearate and 1.7 g of stearic acid were admixed and then tableted by a single-punch tablet press (EK-0, Korsch) such that the fast-disintegrating tablet was 8.5 mm in diameter and weighed 170 mg. Immediately after tableting, tablet hardness was about 1.2 Kp. After completion of tableting, the product was held at room temperature (about 25° C., 10 to 30% RH) for 2 days and then packaged. Physical properties of the packaged tablet were as follows: hardness, 1.2 Kp; friability, 4.5%; disintegration time in water, 50 seconds; disintegration time in the oral cavity, 47 seconds; loss-on-drying value of the tablet, 0.75%; loss-on-drying value of the crushed tablet, 0.79%.

Comparative Example 3

Use of Spray-Dried Mannitol, Dry Binder (Fructose) and 30% Sucrose Solution But High Loss-on-Drying Value 302.5 g of spray-dried mannitol (Mannogem™ EZ, SPI) and 15.9 g of fructose (Fructofin, Danisco) as a dry binder were added to a 3 L high-speed mixer, and 58.1 g of 30% (w/w) sucrose (Samyang Corporation) solution (ethanol:water=4:6 (w:w)) was added thereto and kneaded with rotational mixing at an impeller speed of 150 rpm and a chopper speed of 1,700 rpm. After removal, the product was granulated by passing through a 30-mesh sieve (mesh size: 600 μm), and dried in a 50° C. oven for a relatively short time, about 35 minutes. Drying time was appropriately controlled such that the loss-on-drying value of the final granule was about 5.5%. The final loss-on-drying value of the granules was 5.42% (equivalent to a 6.2-fold loss-on-drying value as compared with the sufficiently dried granules having a corresponding composition).

324.7 g of the manufactured slightly wetted granules, 10.2 g of low-substituted hydroxypropyl cellulose (L-HPC), 3.4 g of calcium stearate and 1.7 g of stearic acid were admixed, and then tableted by a single-punch tablet press (EK-0, Korsch) such that the fast-disintegrating tablet was 8.5 mm in diameter and weighed 170 mg. But tableting was impossible because sticking occurred markedly during tableting.

As known from the above Examples and Comparative Examples, while all of the Examples showed good hardness and low friability as well as fast disintegration, Comparative Example 1, which has mannitol powder instead of spray-dried mannitol, was good in terms of disintegrating time but had low hardness and high friability. Comparative Example 2, which has sufficiently dried granules instead of slightly wetted granules, exhibited low hardness, high friability and long disintegration time. In the case of Comparative Example 3, a sticking problem occurred due to its excessively high loss-on-drying value, which made it impossible to manufacture a normal tablet.

Example 9

Use of Loratadine, Spray-Dried Mannitol, Dry Binder (Fructose) and 50% Sucrose Solution 10 g of loratadine, 152.1 g of spray-dried mannitol (Mannogem™ EZ, SPI), 8.6 g of fructose (Fructofin, Danisco) as a dry binder and 0.3 g of sodium chloride as a flavoring agent were added to a 1 L high-speed mixer, and 35 g of 50% (w/w) sucrose (Samyang Corporation) solution (ethanol:water=4:6 (w:w)) was added thereto and kneaded with rotational mixing at an impeller speed of 130 rpm and a chopper speed of 2400 rpm. After removal, the product was granulated by passing through a 30-mesh sieve (mesh size: 600 μm) and dried in a 50° C. oven for about 45 minutes. Drying time was appropriately controlled such that the loss-on-drying value of the final slightly wetted granules was about 1.8%. The final loss-on-drying value of the slightly wetted granules was 1.82%.

188.5 g of the manufactured slightly wetted granules, 8.0 g of sodium starch glycolate, 1.5 g of sodium stearyl fumarate and 1.5 g of stearic acid were admixed and then tableted by a single-punch tablet press (EK-0, Korsch) such that the fast-disintegrating tablet was 9.5 mm in diameter and weighed 200 mg. Immediately after tableting, tablet hardness was about 1.3 Kp. After completion of tableting, the product was held at room temperature (about 25° C., 10-30% RH) for 2 days and then packaged. Physical properties of the packaged tablet were as follows: hardness, 4.6 Kp; friability, 0.16%; disintegration time in water, 30 seconds; disintegration time in the oral cavity, 25 seconds; loss-on-drying value of the tablet, 1.20%; loss-on-drying value of the crushed tablet, 1.32%.

Example 10

Use of Ondansetron, Spray-Dried Mannitol, Dry Binder (Lactose) and 50% Sucrose Solution 8 g of ondansetron, 152.1 g of spray-dried mannitol (Mannogem™ EZ, SPI), 8.6 g of lactose (Pharmatose 200M, DMV) as a dry binder and 0.3 g of sodium chloride as a flavoring agent were added to a 1 L high-speed mixer, and 35 g of 50% (w/w) sucrose (Samyang Corporation) solution (ethanol:water=4:6 (w:w)) was added thereto and kneaded with rotational mixing at an impeller speed of 140 rpm and a chopper speed of 1800 rpm. After removal, the product was granulated by passing through a 30-mesh sieve (mesh size: 600 μm) and dried in a 50° C. oven for about 45 minutes. Drying time was appropriately controlled such that the loss-on-drying value of the final slightly wetted granules was about 1.8%. The final loss-on-drying value of the slightly wetted granules was 1.78%.

117.0 g of the manufactured slightly wetted granules, 8.0 g of sodium starch glycolate, 1.5 g of sodium stearyl fumarate and 1.5 g of stearic acid were admixed and then tableted by a single-punch tablet press (EK-0, Korsch) such that the fast-disintegrating tablet was 9.5 mm in diameter and weighed 200 mg. Immediately after tableting, tablet hardness was about 1.2 Kp. After completion of tableting, the product was held at room temperature (about 25° C., 10-30% RH) for 2 days and then packaged. Physical properties of the packaged tablet were as follows: hardness, 4.0 Kp; friability, 0.3%; disintegration time in water, 31 seconds; disintegration time in the oral cavity, 27 seconds; loss-on-drying value of the tablet, 0.53%; loss-on-drying value of the crushed tablet, 0.57%.

Example 11

Use of Ramosetron HCl, Spray-Dried Mannitol, Dry Binder (Lactose) and 50% Sucrose Solution 0.08 g of ramosetron HCl, 104.4 g of spray-dried mannitol (Mannogem™ EZ, SPI), 2.74 g of corn starch as a dry binder and 2.74 g of fructose (Fructose, Amresco) as another dry binder, 0.22 g of acesulfame potassium as a sweetening agent and 1.3 g of TiO2 as an antioxidant were added to a 1 L high-speed mixer, and 30.6 g of 50% (w/w) sucrose (Samyang Corporation) solution (ethanol:water=4:6 (w:w)) was added thereto and kneaded with rotational mixing at an impeller speed of 130 rpm and a chopper speed of 2,000 rpm. After removal, the product was granulated by passing through a 30-mesh sieve (mesh size: 600 μm) and dried in a 50° C. oven for about 45 minutes. Drying time was appropriately controlled such that the loss-on-drying value of the final slightly wetted granules was about 1.0%. The final loss-on-drying value of the slightly wetted granules was 1.03%.

188.5 g of the manufactured slightly wetted granules, 10.2 g of low-substituted hydroxypropyl cellulose (L-HPC), 3.4 g of calcium stearate and 1.7 g of stearic acid were admixed and then tableted by a single-punch tablet press (EK-0, Korsch) such that the fast-disintegrating tablet was 8.5 mm in diameter and weighed 170 mg. Immediately after tableting, tablet hardness was about 1.4 Kp. After completion of tableting, the product was held at room temperature (about 25° C., 10-30% RH) for 2 days and then packaged. Physical properties of the packaged tablet were as follows: hardness, 3.8 Kp; friability, 0.35%; disintegration time in water, 28 seconds; disintegration time in the oral cavity, 18 seconds; loss-on-drying value of the tablet, 0.43%; loss-on-drying value of the crushed tablet, 0.51%.

Example 12

Use of Simvastatine, Spray-Dried Mannitol, Dry Binder (Fructose) and 50% Sucrose Solution 20 g of simvastatine, 136 g of spray-dried mannitol (Mannogem™ EZ, SPI), 6.23 g of fructose (Fructofin, Danisco) as a dry binder, 2.08 g of corn starch as a dry binder and 0.31 g of sodium chloride as a flavoring agent were added to a 1 L high-speed mixer, and 42.6 g of 50% (w/w) sucrose (Samyang Corporation) solution (ethanol:water=4:6 (w:w)) was added thereto and kneaded with rotational mixing at an impeller speed of 150 rpm and a chopper speed of 2,500 rpm. After removal, the product was granulated by passing through a 30-mesh sieve (mesh size: 600 μm) and dried in a 50° C. oven for about 45 minutes. Drying time was appropriately controlled such that the loss-on-drying value of the final slightly wetted granules was about 1.8%. The final loss-on-drying value of the slightly wetted granules was 1.81%.

191.3 g of the manufactured slightly wetted granules, 6.0 g of sodium starch glycolate and 3.0 g of sodium stearyl fumarate were admixed and then tableted by a single-punch tablet press (EK-0, Korsch) such that the fast-disintegrating tablet was 12.0 mm in diameter and weighed 400 mg. Immediately after tableting, tablet hardness was about 2.3 Kp. After completion of tableting, the product was held at room temperature (about 25° C., 10-30% RH) for 2 days and then packaged. Physical properties of the packaged tablet were as follows: hardness, 5.6 Kp; friability, 0.46%; disintegration time in water, 33 seconds; disintegration time in the oral cavity, 20 seconds; loss-on-drying value of the tablet, 0.86%; loss-on-drying value of the crushed tablet, 0.94%.

The invention claimed is:
1. A fast-disintegrating tablet, comprising slightly wetted granules that comprise a spray-dried mannitol and a sucrose binder, and have 1.05- to 5-times greater loss-on-drying than sufficiently dried granules,
   wherein the fast-disintegrating tablet has the following properties (1) to (4);
   (1) hardness of 4.0 Kp or more;
   (2) friability of 0.5% or less;
   (3) disintegration time in water of 1 minute or less; and
   (4) disintegration time in an oral cavity of 30 seconds or less.
2. The fast-disintegrating tablet according to claim 1, wherein the slightly wetted granules further comprise a dry binder.
3. The fast-disintegrating tablet according to claim 2, wherein the dry binder is selected from the group consisting of saccharide, sugar alcohol, starch, polysaccharide, cellulose derivative and a mixture thereof.
4. The fast-disintegrating tablet according to claim 1, wherein the spray-dried mannitol is comprised in an amount of 20 to 98% by weight, based on 100% by weight of the slightly wetted granules.
5. The fast-disintegrating tablet according to claim 1, wherein the sucrose binder is comprised in an amount of 1 to 50 parts by weight as a dried sucrose, based on 100 parts by weight of the spray-dried mannitol.
6. The fast-disintegrating tablet according to claim 2, wherein the dry binder is comprised in an amount of 50 or lower parts by weight, based on 100 parts by weight of the spray-dried mannitol.
7. The fast-disintegrating tablet according to claim 1, which further comprises an active ingredient.
8. A process for manufacturing a fast-disintegrating tablet according to claim 1, comprising the steps of:
   forming granules comprising a spray-dried mannitol and a sucrose binder;
   drying the granules to obtain slightly wetted granules having 1.05- to 5-times greater loss-on-drying value than sufficiently dried granules;
   forming a post-granulation mixture for tableting comprising the slightly wetted granules;
   compressing the post-granulation mixture under a pressure of 150 Mpa or less to obtain a tablet; and
   drying the tablet.
9. The process for manufacturing the fast-disintegrating tablet according to claim 8, wherein the sucrose binder is used in a dissolved state in water, non-aqueous solvent or a mixed solvent thereof.
10. The process for manufacturing the fast-disintegrating tablet according to claim 9, wherein the concentration of sucrose is 1 to 60% (w/w), based on water, non-aqueous solvent or a mixed solvent thereof.
11. The fast-disintegrating tablet according to claim 1, wherein the amount of slightly wetted granules is 50 to 99% by weight, based on 100% by weight of the tablet.
12. The process for manufacturing the fast-disintegrating tablet according to claim 8, wherein the step of drying is conducted:
   under the condition of temperature of 20 to 30° C. and relative humidity of 40% or less;
   in a 20° C.- to 50° C.-convection oven;
   by providing dry air; or
   by using a dehumidifier or dehumidifying agent.

* * * * *